(12) United States Patent
Pal et al.

(10) Patent No.: US 12,426,781 B2
(45) Date of Patent: Sep. 30, 2025

(54) PORTABLE RETINAL IMAGING SYSTEM

(71) Applicant: FORUS HEALTH PVT. LTD., Bangalore (IN)

(72) Inventors: Sourav Pal, Bangalore (IN); Venkatakrishnan Srinivasan, Bangalore (IN)

(73) Assignee: FORUS HEALTH PVT. LTD. (IN)

( * ) Notice: Subject to any disclaimer, the term of this patent is extended or adjusted under 35 U.S.C. 154(b) by 157 days.

(21) Appl. No.: 17/787,295

(22) PCT Filed: Jun. 23, 2021

(86) PCT No.: PCT/IN2021/050610
§ 371 (c)(1),
(2) Date: Sep. 15, 2022

(87) PCT Pub. No.: WO2022/190113
PCT Pub. Date: Sep. 15, 2022

(65) Prior Publication Data
US 2024/0108218 A1   Apr. 4, 2024

(30) Foreign Application Priority Data

Mar. 10, 2021   (IN) .............................. 202141010092

(51) Int. Cl.
*A61B 3/12* (2006.01)
*A61B 3/00* (2006.01)

(52) U.S. Cl.
CPC .......... *A61B 3/1241* (2013.01); *A61B 3/0008* (2013.01); *A61B 2503/045* (2013.01)

(58) Field of Classification Search
CPC ................ A61B 3/1241; A61B 3/0008; A61B 2503/045

(Continued)

(56) References Cited

U.S. PATENT DOCUMENTS 8,836,778 B2   9/2014 Ignatovich
2006/0146284 A1*   7/2006 Collins ................ A61B 3/1208
351/215

(Continued)

FOREIGN PATENT DOCUMENTS

KR   2020-0093502 A   8/2020
WO   2020/188007 A1   9/2020

OTHER PUBLICATIONS

Indian Office Action dated Jan. 24, 2024 as received in application No. 202141010092.

*Primary Examiner* — Sharrief I Broome

(57) ABSTRACT

Preterm babies have a high risk of retinopathy. Doctors conduct fundus fluorescein angiography to determine the state of the blood vessels in their retinas. Disclosed is a system (100) for conducting fundus fluorescein angiography configured for light weight, small size, and providing a sharp, high contrast angiograph. The disclosed system uses a moulded annular light source, blue and white LEDs (120) for providing the illumination, an planar annular emission filter (125) for filtering the blue light, and imaging optics (130) configured for reducing aberration. The imaging optics (130) comprises a mechanical iris (136) to control the amount of light reaching an image sensor (150), a tuneable liquid lens (141) for focusing the image, a green barrier filter (146) that may be removed from the path of the light—for conducting fundus photography. The white LEDs and the mechanical iris (136) may be used for conducting fundus photography.

6 Claims, 7 Drawing Sheets

(58) Field of Classification Search
USPC .......................................................... 351/206
See application file for complete search history.

(56) References Cited

U.S. PATENT DOCUMENTS

| | | |
|---|---|---|
| 2010/0073633 A1 | 3/2010 | Uchida et al. |
| 2012/0044458 A1* | 2/2012 | Iwanaga .................. A61B 3/12 |
| | | 351/207 |
| 2012/0287255 A1* | 11/2012 | Ignatovich ........... A61B 3/1208 |
| | | 348/78 |
| 2013/0033593 A1* | 2/2013 | Chinnock ................ A61B 3/14 |
| | | 348/78 |
| 2013/0057828 A1* | 3/2013 | de Smet .................. A61B 3/12 |
| | | 351/207 |
| 2018/0220887 A1* | 8/2018 | Kanamori ................ A61B 3/12 |
| 2019/0110677 A1* | 4/2019 | Walsh ...................... A61B 3/12 |

* cited by examiner

PORTABLE RETINAL IMAGING SYSTEM

FIELD OF THE DISCLOSURE

This disclosure belongs to the field of medical systems. In particular, it belongs to the field of ophthalmic systems. Still particularly, it belongs to the field of systems for fundus imaging.

BACKGROUND TO THE DISCLOSURE

Babies born much before the completion of the gestation period are referred to as premature babies and abbreviated to preemies. These babies are prone to many adverse medical conditions including ophthalmic ones. One such disorder is called retinopathy of prematurity (ROP) that can cause lifelong visual impairment or even permanent blindness.

This condition is observed in babies with a birth weight of 1250 grams or less or born before a gestation period of thirty-one weeks whereas the full term is thirty-eight to forty-two weeks. In ten percent of the cases in which ROP is observed, the condition leaves a permanent visual impairment or blindness.

ROP is caused by the growth of abnormal blood vessels that grow and that spread throughout the retina, the tissue that lines the back of the eye. These abnormal blood vessels are fragile. They can leak and scar the retina and detach it from its normal position. This condition, called retinal detachment, is the main cause of visual impairment and blindness in ROP.

The retina is a layer of tissue that lines the back of the inside of the eye. It is located near the optic nerve. The function of the retina is to receive light that the lens of the eye has focused on it, convert the light into neural signals, and send these signals through the optic nerve to the brain for seeing images.

Methods and systems have been developed to photograph the blood vessels in the retina. Such systems are called fundus imaging systems and one may use the technique called fundus fluorescein angiography. In this technique the subject is injected with a dye(?). The fundus is then illuminated with a blue light. This blue light reacts with the dye in the blood in the blood vessels in the retina and emit green light. The emitted light is photographed so that all the blood vessels are clearly visible. This photograph helps doctors and ophthalmologists in assessing the state of the blood vessels and take necessary action for preventing visual impairment in the subject. This may include administering suitable drugs to help the condition.

The procedure may be repeated to assess the effect of the drugs and manage the condition effectively.

Prior art patent literature teach various solutions for obtaining a compact light weight camera suitable for neonatal use. All of them suffer from at least one drawback with reference to weight, energy efficiency, maneuverability, ease of operation, quality of image produced, and so on.

SUMMARY OF THE DISCLOSURE

This summary is provided to introduce a selection of concepts in a simplified format that are further described in the detailed description of the invention. This summary is not intended to identify key or essential inventive concepts of the subject matter, nor is it intended for determining the scope of the invention.

Thus, with reference to the state of the art, there has been long felt need for a system that mitigates or overcomes one or more of the problems in the state-of-the-art systems. It is an aim of the present disclosure to disclose a system that is light in weight. Another aim of the present disclosure is to disclose a system that is compact such that it is easier to use it on a neonatal premature baby. Another aim of this disclosure is to disclose a system that is easier to manoeuvre. Yet another aim of the present disclosure is to disclose a system that is energy efficient. One more aim of the disclosure is to disclose a unit that is easier to operate. Another aim of the disclosure is to disclose a system that may be used to conduct both fundus fluorescein angiography and Fundus photography without making any changes to the system manually. Yet another aim is to provide a system the images from which have reduced distortion than possible at present. An additional aim of this disclosure is to disclose a system that enables fluorescein angiographic images with improved contrast and hence providing better or more information to an eye specialist who views or analyses the images. A further aim of the disclosure is to disclose a single system that can not only perform Fundus Fluorescein Angiography and Fundus photography on a neonatal subject but also on older subjects. The difference therein is as follows. In premature babies and other neonatal babies, the crystalline lens in the eye is not yet formed. Whereas in older subjects, the crystalline is formed and that leads to reflection of light from the surface of the lens creating artefacts in the captured images. The aim of the present disclosure is to disclose a system that has measures to eliminate or at least mitigate this problem but still achieving the other stated aims of the disclosure.

These aims are achieved by the measures recited hereinafter. An imaging system configured for carrying out fundus imaging on a neonatal subject is provided. The system employs a moulded light guide to form an annular light source making the system light and compact. The source of light for the annular light source are LEDs, helping to make the system light and also compact. The LEDs used are of both white light emitting and blue light emitting LEDs. This makes the system suitable for both Fundus photography and Fundus Fluorescein Angiography. Additionally, the source of light employs a plurality of LEDs wherein, the plurality of LEDs is arranged in a circle to match with the circular input end of the moulded light guide and the alternate LEDs are blue and white light LEDs. Further, a planar annular filter is provided between the LEDs and wherein the annular filter has alternate blue and colourless sections so arranged that the blue section filters the light emitted by the blue LEDs and the clear sections allow the light emitted by the white LEDs unaltered or unfiltered. Further the sections for filtering the blue light have a low pass characteristic cutting off the wavelengths closer to green light. The system further has a contact lens for being in contact with the cornea of the subject's eye to direct the annular light into the fundus of the subject's eye. The system further employs a green barrier filter in the path of the light from the eye for filtering subject before it reaches the reaching an image sensor that captures an image. The green barrier filter has a high pass characteristic such that it cuts off light of wavelengths closer to the wavelengths of blue light. This helps in increasing the contrast of the angiographic image. Further, the position of the green barrier filter is motor controlled for inserting and removing it from a path of light between the eye of the subject and the image sensor. This enables the same disclosed system to be used for both fundus fluorescein angiography and Fundus photography without making any changes to the system manually.

Thus, in summary, disclosed is an imaging system configured for carrying out the dual functions of fundus fluorescein angiography on a preterm baby subject and fundus imaging on a subject's eye, the system characterised by a moulded light guide based annular light source, a source of light for the light guide, the source of light comprising a plurality of LEDs, the plurality of LEDs being arranged in a circle wherein, alternate LEDs are blue light emitting LEDs and white light emitting LEDs; a planar annular emission filter positioned between the light guide and the plurality of LEDs for filtering the light emitted by the blue light emitting LEDs to reach the light guide and for allowing light emitted by the white light emitting LEDs to reach the light guide unfiltered; a green barrier filter, for filtering light reflected by the fundus of the subject's eye, before the light reaching an image sensor, and wherein the position of the green barrier filter is motor controlled for inserting and removing the green barrier filter from the optical axis of the imaging optics; an aperture unit for controlling an amount of light reaching the image sensor; a liquid lens, a focal length of which may be varied by applying one or more voltages to electrodes of the liquid lens, for focusing an image on the image sensor; an imaging optics comprising a plurality of lenses configured for focusing an image of the fundus of the subject's eye, wherein the lenses are lenses that bend light rays substantially equally at either surface of each lens for producing a low distortion image on the image sensor; and a control unit configured at least for receiving user inputs for selecting one of white light emitting LEDs and blue light emitting LEDs from the plurality of LEDs, focusing the image on the image sensor through controlling the liquid lens, and inserting or removing the green barrier filter from the optical axis of the imaging optics.

To further clarify advantages and features of the present invention, a more particular description of the invention will be rendered by reference to specific embodiments thereof, which is illustrated in the appended figures.

It is to be appreciated that these figures depict only typical embodiments of the invention and are therefore not to be considered limiting of its scope. The invention will be described and explained with additional specificity and detail with the accompanying figures.

BRIEF DESCRIPTION OF THE FIGURES

The invention will be described and explained with additional specificity and detail with the accompanying figures in which.

Further, skilled artisans will appreciate that elements in the figures are illustrated for simplicity and may not have been necessarily been drawn to scale. Furthermore, in terms of the construction of the system, one or more components of the system may have been represented in the figures by conventional symbols, and the figures may show only those specific details that are pertinent to understanding the embodiments of the present invention so as not to obscure the figures with details that will be readily apparent to those of ordinary skill in the art having benefit of the description herein.

DESCRIPTION OF THE DISCLOSURE

To promote an understanding of the principles of the invention, reference will now be made to the embodiment illustrated in the figures and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

It will be understood by those skilled in the art that the foregoing general description and the following detailed description are exemplary and explanatory of the invention and are not intended to be restrictive thereof.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more systems or sub-systems or elements or structures or components proceeded by "comprises . . . a" does not, without more constraints, preclude the existence of other systems or other sub-systems or other elements or other structures or other components or additional systems or additional sub-systems or additional elements or additional structures or additional components. Appearances of the phrase "in an embodiment", "in another embodiment" and similar language throughout this specification may, but do not necessarily, all refer to the same embodiment.

Unless otherwise defined, all technical and scientific terms used herein have the same meaning as commonly understood by one of ordinary skill in the art to which this invention belongs. The system, methods, and examples provided herein are illustrative only and not intended to be limiting.

Embodiments of the present invention will be described below in detail with reference to the accompanying figures.

Figure 1:
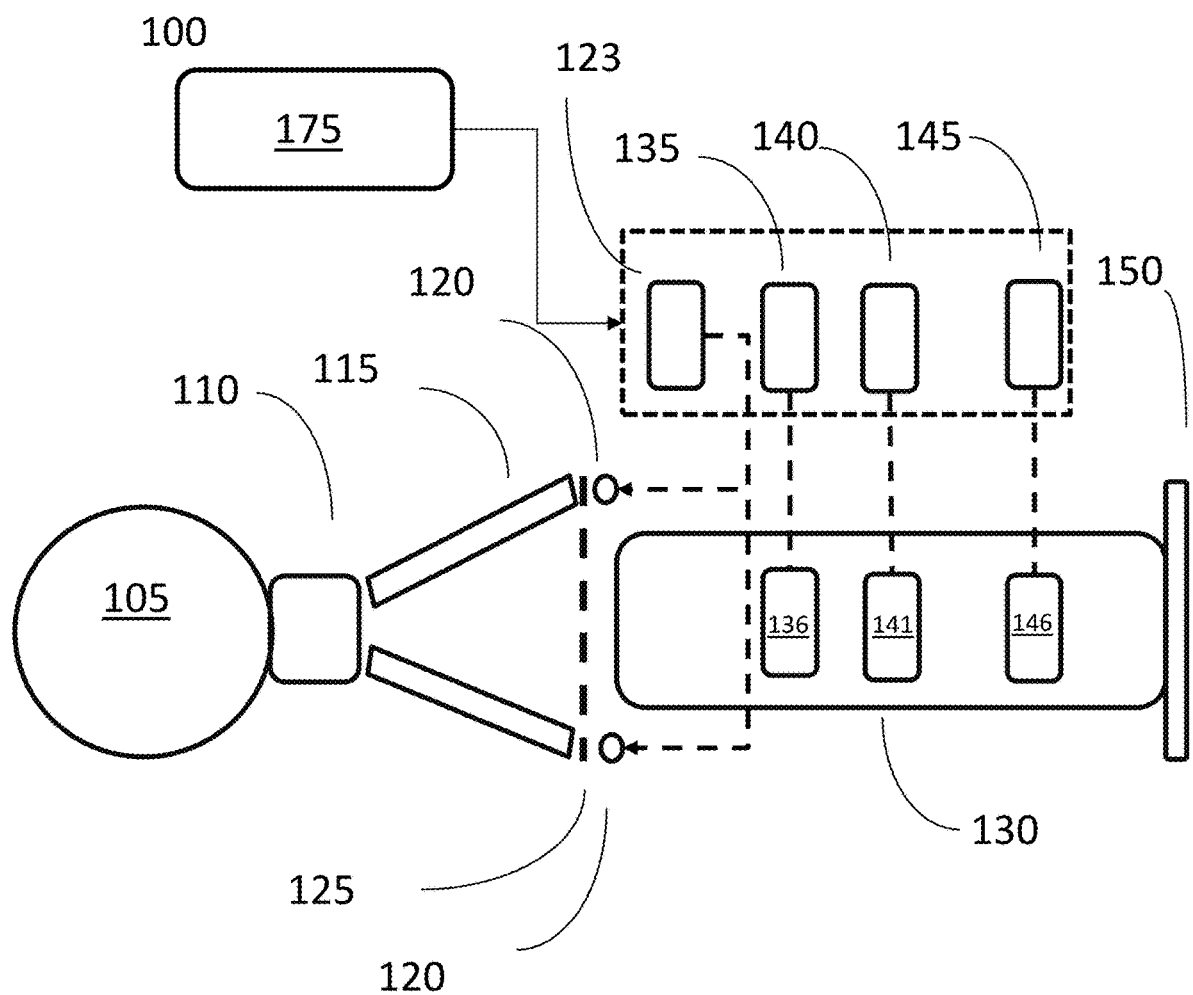
FIG. 1 depicts an overall simplified diagram of one aspect of the disclosed system.

With reference to FIG. 1, the general arrangements of the basic elements of the system 100 disclosed by the present disclosure will now described. The human eyeball or the subject's eyeball under test using the system disclosed herein is represented by 105.

A contact lens 110 is configured for being in contact with the subject's cornea and focusing the light from an annular light source into the subject's eye 105 through its iris. A light guide 115, the shape of which may be described as having a cup shape, is so located that the annular light produced by it enters the contact lens from the side opposite to the side in contact with the subject's cornea. The annular light is produced by a plurality of LEDs 120 arranged in a circle so that the light emitted by them enters the light guide 115 through its rim. Further, the LEDs 120 are so arranged that alternate LEDs are of white light emitting LEDs and blue light emitting LEDs. The LEDs 120 may be arranged on a printed circuit board for example. Between the LEDs 120 and the light guide 115 is an annular filter 125 with alternating bands of blue and clear filters. The lengths of the blue and clear bands are configured to match the locations of the blue light emitting and white light emitting LEDs respectively. The light rays entering the cup shaped light guide undergo total internal reflection at the walls of the light guide 115 and emerge from the other rim of the light guide 115, thus forming an annular light.

Once the arrangement described above is made to shine an annular light into the eye 105 through the contact lens 110 and then through the iris of the subject, the fundus of the eye 105 is illuminated substantially uniformly. The wall of the eye opposite to the iris reflects the incident light. This in turn enters the contact lens 110 from its side in contact with the cornea and exits the contact lens 110 from the opposite side. This light is collected by an arrangement of lenses, in general referred to as the imaging optics 130 that focuses the light to form a real image on an image sensor 150 located at the image plane of the imaging system. The details of the imaging optics 130 will be described in detail with reference to FIG. 5 further. The image sensor 150, a charge coupled device or a CMOS image sensor, for example, is configured to capture the image of the wall of the subject's eye 105, opposite to the iris.

In the path of the light through the imaging optics 130, the amount of light reaching the image sensor 150 may be controlled by an aperture unit 136, the aperture of which may be controlled either by a mechanical arrangement or a motorised gear unit 135. Next in the path of the light through the imaging optics 130 is a tuneable liquid lens 141, the focal length of which may be controlled by application of voltages to its electrodes. A control unit 140 is configured for applying suitable voltages to alter the focal length of the liquid lens 141, in a known way. A green barrier filter 146 is placed in the path of the light for filtering the light that has passed through the liquid lens 141. The green barrier filter 146 can be inserted into the optical axis or removed. The details of the green barrier filter 146 and the mechanical arrangement will be described further with reference to FIG. 6.

Now the general principles of fundus fluorescein angiography are described, still with reference to FIG. 1, for a basic understanding. A detailed description follows that points out the advantageous features of the disclosed system for fundus fluorescein angiography.

Figure 2:
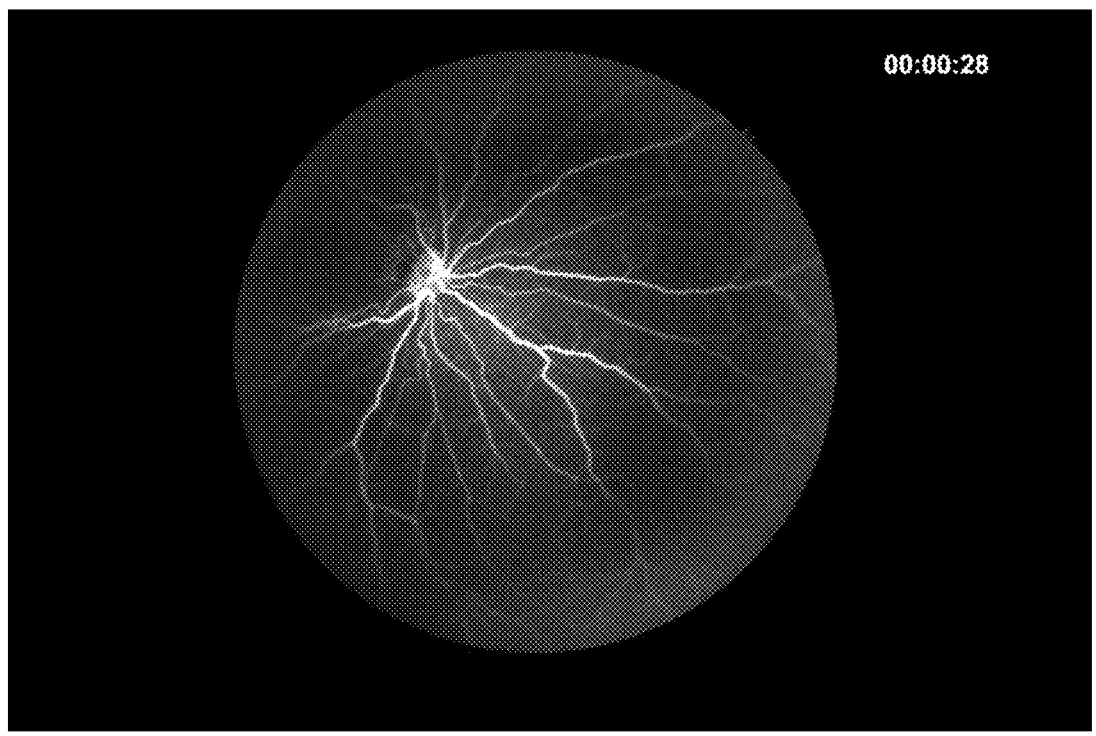
FIG. 2 shows a typical retinal angiograph of a human eye.

The subject, a preterm baby for example, is injected with a dye called fluorescein sodium ($C_{20}$ $H_{10}$ $Na_2$ $O_5$), for example. An annular light is produced by the lightguide 115 by guiding the light from LEDs 120 through total internal reflection. The LEDs 120 used for this are the blue light emitting LEDs and the white light emitting ones remain unenergized. This may be controlled by a switch or other control circuit 123. The dye mixed in the blood of the subject coursing through the blood vessels of the retina of the subject's eye 105 absorbs the blue light it receives and emits green light. The parts surrounding the blood vessels may reflect the blue light they receive as it is, with only a part of it absorbed or scattered in other ways. This light is collected by the contact lens 110 and the imaging optics 130 and an image is formed on the image sensor 150. However, this light, which is a mixture of green and blue light is filtered with a green barrier filter 146. This ensures that, whereas light reflected by the rest of the retina is filtered off, the blood vessels alone glow with the green light and hence the image sensor 150 senses an image wherein the blood vessels alone standout in white, for example, and the rest of the areas of the retina are dark or black. Using these principles, producing a sharp and high contrast image is one of the objectives of the disclosed system. An example of such an angiogram is shown in FIG. 2. Other objectives will be mentioned along with the description of the other embodiment and features of the disclosed system.

Various embodiments and features of the disclosed system will now be described in detail. The advantages provided by each will also be described.

Annular Light Source and Filters:

In FIG. 4a, the eye of the subject is shown here as 405. The light guide is shown as 415 and the LEDs as 420. Since it is a sectional view, only two LEDs 420 are shown. FIG. 4b shows the LEDs 420 arranged in a circle. The LEDs are shown as squares out of which the black squares represent blue light emitting LEDs and the grey squares represent white light emitting LEDs. FIG. 4c shows the annular filter 425. The white parts of the annular filter 425 are the clear parts of the filter that allows the light from the white LEDs to enter the light guide 415 unfiltered whereas the grey parts of the annular filter 425 represent the blue filter that filters the light emitted by the blue light emitting LEDs. This filter that filters the blue light may also be referred to as the excitation filter as the light filtered by it is used for exciting the fluorescein in the blood of the subject coursing through the blood vessels in the retina of the subject.

Figure 3:
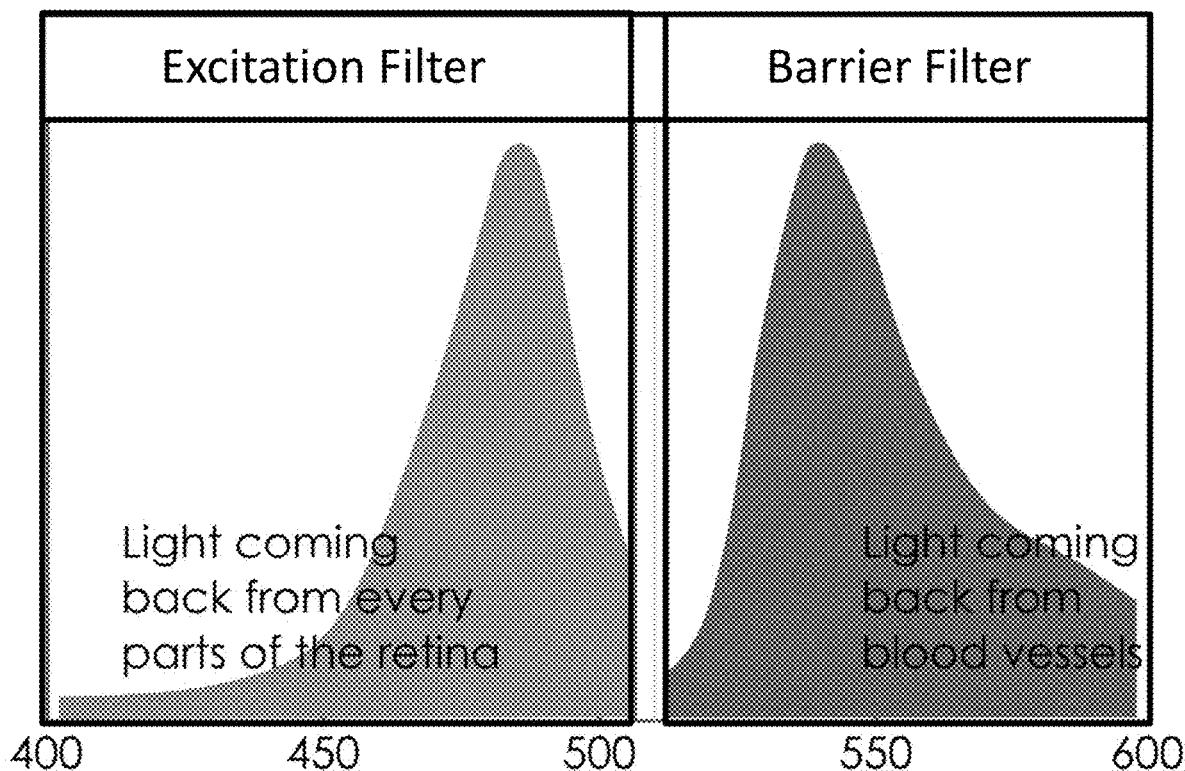
FIG. 3 shows diagrammatic representation of the physical phenomenon on which fundus fluorescein angiography is based.

The excitation filter 125 is a low pass filter as shown in FIG. 3. The light source, blue light emitting LEDs of LEDs 120 for example, emit light with wavelengths between 430 nm and 520 nm with a maximum energy at around 480 nm. Maximum absorption of this energy by fluorescein that is injected into the blood of the subject is between 465 nm and 490 nm, based on the pH of the blood. This almost matches with emission peak of the blue light source—the blue light emitting LEDs of LEDs 120. Subsequent to absorption of blue light, fluorescein emits light in the green wavelengths band, that is, in the wavelength range of 510 nm to 560 nm. Thus, there is a band of wavelengths that overlap. This may reduce the contrast in the final angiographic image. To mitigate this, the blue excitation filter 525 has a cut off wavelength substantially at 500 nm. That means that it allows blue light having wavelengths up to a maximum of 500 nm. Correspondingly, the green barrier filter 146 has a lower cut off wavelength above 500 nm, say 515 nm, for example. This ensures that the green light reaching the image sensor 150 of FIG. 1 has no stray light reflected from the subject's eye in the blue wavelengths. This arrangement of filters provides the advantage that the image produced may have a higher contrast than would otherwise be possible.

Figure 4:
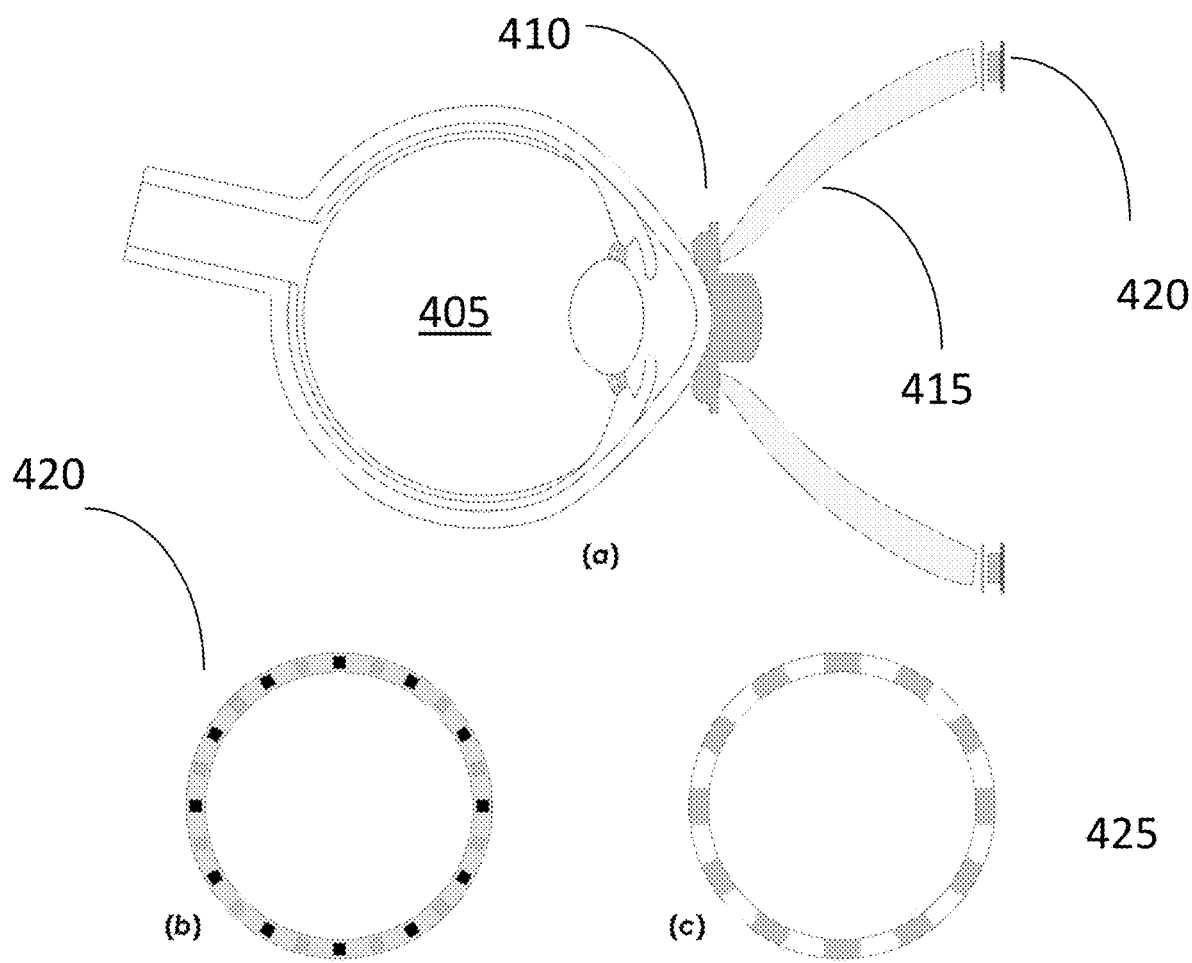
FIG. 4 shows the arrangement of the illuminating part of the disclosed system according to one aspect of the disclosed system.

Further, still with reference to FIG. 1, and additionally with reference FIG. 4, the use of the moulded light guide 115 will be described. It helps in reducing the weight of the overall system since it is made of polycarbonate and has a low weight. The use of LEDs 120 also reduces the weight, compared to optic fibre based annular light sources for example or light guides that need a large number of LEDs to obtain the required brightness of the illumination. This is not only because the LEDs in general are light but also because they are highly energy efficient and the power supply requirement of the system 100 is also reduced because of the smaller number of LEDS 120. Still further, the introduction of the annular filter 125 between the LEDs 120 provides the advantage of making the system 100 more compact and provides the advantage of making it easier to use it on neonates and premature babies.

Imaging Optics

Figure 5:
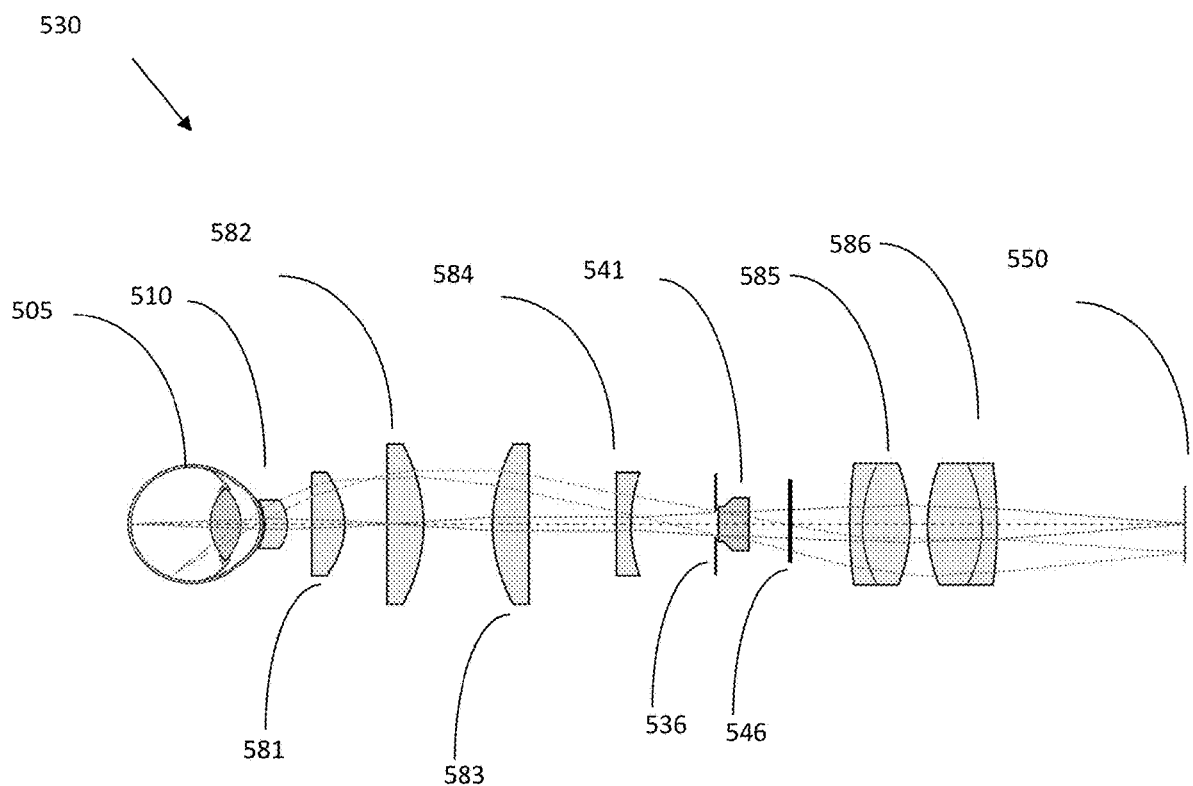
FIG. 5 shows a representation of one embodiment of the optical system for capturing the image of the retina according to one aspect of the present disclosure.

Now, the imaging optics 130 that was first described briefly with reference to FIG. 1 will be descried in detail with reference to FIG. 5. The imaging optics 530 comprises contact lens 510 that is in contact with the cornea of the subject's eye 505. Contact between the contact lens 510 and the cornea is established using a gel of refractive index matching the refractive index of the cornea. An image sensor 550 is positioned at the image plane for capturing the image digitally. Plano-convex lenses 581, 582 and 583 are lenses that work together with contact lens 510 to ensure the required field of view. The plano-concave lens 584 acts as a field-flattener and takes part in deciding the entrance pupil of the system. It also plays a significant role in removal of artefacts from the image. Green barrier filter 546 is positioned just after the tuneable liquid lens 541, in the path of the light, where the diameter of the image forming beam of light is small such that a green barrier filter of a reasonably small diameter may be accommodated. Diameter of the circular filter is just enough to allow the incoming beam of light. The actual arrangement of the motorized filter is shown in FIG. 6 and described with reference to it.

The tuneable liquid lens 541 is for focusing a real image at the image plane where the image sensor 550 is located. The tuneable liquid lens 541 thus focuses an image that may otherwise be unfocused by different refractive powers of different subject's eyes. Two doublet lenses 585 and 586 determine the size of the final image, which is limited by the size of the image sensor 550. Moreover, the two doublet lenses 585 and 586 correct any residual aberration from the remaining lenses, described hitherto. This arrangement of lenses in the imaging optics 530 provides the following advantages. This arrangement of lenses reduces aberrations or artefacts in the final image projected on the image sensor 550. The inventors have realised that this effect may be achieved by using lenses in which light rays are bent substantially evenly by the two surfaces of each lens. Further, this arrangement also reduces the overall length of the system. This also has the advantageous effect that it eliminates the need for folding of an imaging system that may otherwise be needed. This in turn makes the system more manoeuvrable, which is especially advantageous while using on neonates and premature babies.

Figure 6:
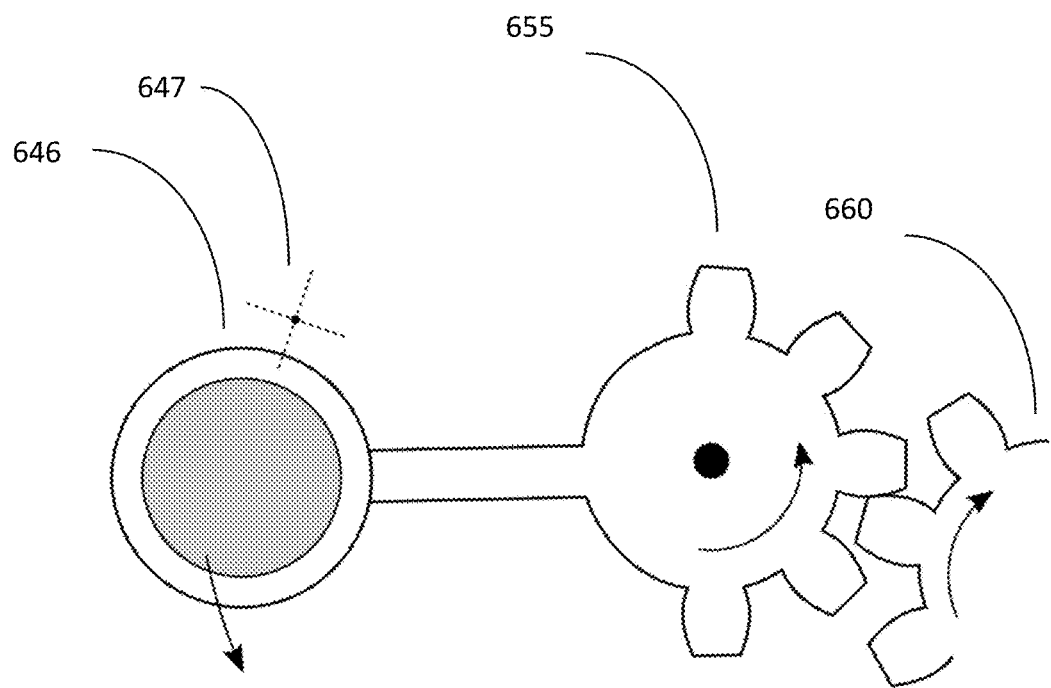
FIG. 6 shows one implementation of a mechanical arrangement for positioning or removing a green filter from the optical path.

FIG. 6 shows an embodiment of the means for bringing the green barrier filter 646 in and out of the path of the light reflected from the eye 505 of the subject. The green barrier filter 646 is attached to an arm of a gear 655. A motorised gear unit 660 drives the gear 655. A clockwise and an anti-clockwise rotation of gear 655 moves the green barrier filter in anti-clockwise and clockwise direction, respectively. Therefore, a clockwise rotation of the motorised gear unit 660 takes filter away from the optical axis of the imaging optics 530 depicted as the intersection point 647 of two dotted lines. An anti-clockwise rotation of the motorised gear unit 660 places the filter 646 coaxially with the imaging optics 130. The motor unit may be driven by signal provided by a user of the disclosed system.

The purpose of moving the green barrier filter 146 into the optical axis or move it away from it and the need for the white LEDs in the annular light source is as follows. When the disclosed system is used for carrying out Fluorescein Fundus Angiography, the blue light emitting LEDs alone among the LEDs 120 are energised and emit the blue light required. And as explained earlier, the blue areas of the annular filter 125 filters the blue light as a low pass filter. The fluorescein dye in the subject's blood coursing through the blood vessels of the retina absorbs this blue light and fluoresces green light. The imaging optics 130 directs this green light towards the image sensor 150. By moving the green barrier filter 146 into the optical axis this green light is filtered, and a real image is formed at the image plane to be captured by the image sensor 150.

However, the same disclosed system 100 may also be used for normal fundus photography, when needed. During that function, only the white light emitting LEDs among the LEDs 120 are energised through the control unit 123 and the green barrier filter 146 is moved away from the optical axis. This enables normal fundus photography. Further the aperture unit 136 may then be controlled to increase or decrease the aperture to obtain a most suitable photograph. In any case, while conducting fundus fluorescein angiography This is because the crystalline lens of the eye is not yet formed in preterm babies or neonates. On the other hand, while conducting fundus imaging in older subjects, there is a likelihood of such unwanted reflected light from the crystalline lens of the eye of the subject. In such cases the aperture of the aperture unit 136 may be controlled to allow only a required amount light to reach the image senor 150, to obtain a clear picture. Thus, the disclosed system offers the advantage that it is a dual function system and may be used for both fundus fluorescein angiography and normal fundus photography.

Control Unit

Now that the various elements of the disclosed system have been described and the advantages that they offer have been explained, a control unit 175 configured for operating the system will now be described. The control unit 175 is configured for receiving inputs from a user, interpreting the inputs, and acting on the inputs. The control unit 175 is communicatively connected to a user interface unit of the system (not shown).

One user input may be a mode selection. The two modes being fundus fluorescein angiography and fundus photography. If the user input is for fundus fluorescein angiography mode, the controller energises the blue light emitting LEDs of the plurality of LEDs 120. At the same time, it controls the position of the green barrier filter 146 by driving the motorized gear unit 660 such that the green barrier filter 146 is in the optical axis of the imaging optics 130. At the same time, it may also increase the aperture of the mechanical iris 536 to the maximum diameter to let not reduce the light received from the eye 105 of the subject.

On the other hand, if the selectin is fundus photography mode, the control unit 175 deenergized the blue light emitting LEDs among the plurality of LEDs 120 and energise the white light emitting LEDs. At the same time, it controls the position of the green barrier filter 146 by driving the motorized gear unit 660 such that the green barrier filter 146 is no longer in the optical axis of the imaging optics 130.

In either case, the control unit 175 will remain active and receive inputs from the user interface unit and controls the aperture of the mechanical iris 136, the focal length of the liquid lens 141 to obtain an image that is focused well on the image sensor 150.

While the description of the system is now complete no detailed execution of the control unit 175 is described herein. This is because a person skilled in the art will be able to execute such a control unit in a multitude of different known ways. For example, the control unit may comprise a microcontroller communicatively connected to a memory wherein the memory stores instructions to be executed by the microcontroller. The user interface may comprise push button switches that send pulse commands to the microcontroller in a known way. As described hitherto the user inputs may comprise the fundus fluorescein angiography mode or fundus photography mode, for example. Or it may be to raise or lower the focal length of the liquid lens. The microcontroller may be configured to sense the user inputs retrieve the instructions from the memory and execute the actions necessary to perform those actions. All such controls are well-known in the art and does not need any elaboration here.

Thus, a wide field imaging system 100 configured for imaging the retina of a human subject's eye 105, is disclosed. The disclosed imaging system 100 comprises an LED based illumination system comprising a plurality of LEDs 120. A moulded waveguide 115, which functions on the principle of total internal reflection, plays a major role in reducing the size, weight, and energy consumption of the disclosed system making it especially suited for use on neonates and premature babes. The illumination system comprises blue light emitting LEDS and white light emitting LEDs 120 for carrying out fundus fluorescein angiography and capturing a colour fundus image respectively. A green barrier filter 146, the position of which is controlled by a motorized gear unit 660 works with blue light emitting LEDs in fundus fluorescein angiography mode. A tuneable focus liquid lens 141 in the imaging optics 130 facilitates focusing a sharp image on the image sensor 150 placed at the image plane of the imaging optics 130. The disclosed system 100 is capable of screening not only preterm or premature babies but also adults as well. A motorized aperture unit 136 located in proximity with the tuneable liquid lens 141 helps in reduction of unwanted reflection from the crystalline lens of an adult eye. The imaging optics 130 is configured for reducing aberrations by using lenses that bend the rays substantially equally at either faces of the lenses.

Mechanical Iris

Figure 7:
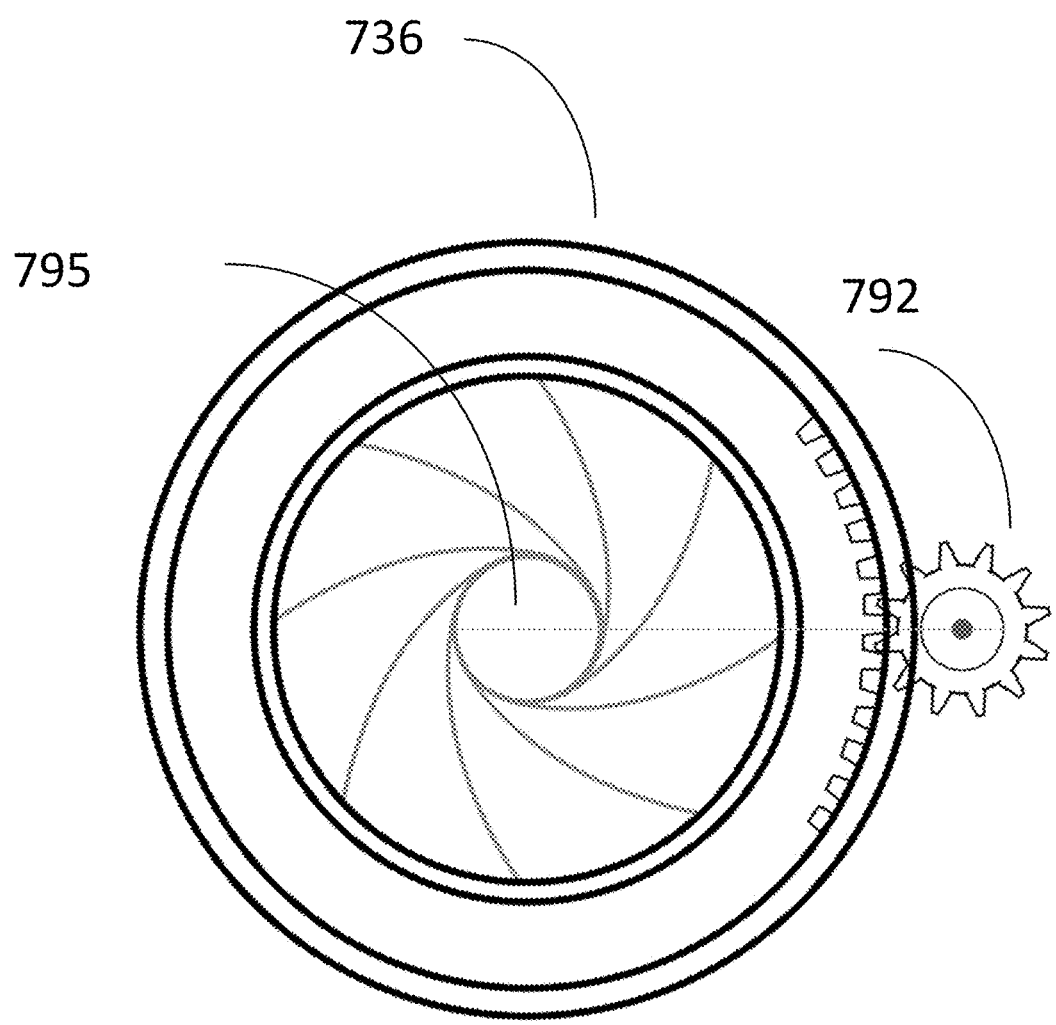
FIG. 7 shows an exemplary aperture control mechanism known in the art, for controlling the aperture and thereby the amount of light reaching the imaging screen.

FIG. 7 shows an exemplary mechanical iris 736. This is a well-known mechanism and is shown here for the sake of completeness. When the geared wheel 792 rotates the diameter of the aperture 795 varies, say it increases when the geared wheel rotates in the clockwise direction the diameter of the aperture 795 increases and vice versa, based on user input received through an user interface unit of the system (not shown).

Further, it should be noted that a variety of variants of the embodiments may be thought of by a person of ordinary skill in the art without deviating from the principles on which this disclosure is based and hence all such modifications are to be treated as embodiments of this disclosure. For example, a person skilled in the art may simplify this and dispose of the second of the dual-purpose system disclosed. That is create a system dedicated to only to carry out fundus fluorescein angiography. That means, eliminate the white light emitting LEDs, the planar annular emission filter 125, the mechanical iris 136, and obtain a compact, fundus fluorescein angiography system suitable for use on preterm babies. For example, the moulded light guide may have other forms but small in size to obtain a compact, fundus fluorescein angiography system suitable for use on preterm babies. Still further, the planar annular emission filter 125, may be eliminated and the moulded light guide 115 may be coated with a blue filtering die to have the same effect. It may also be possible to make a single purpose system by eliminating the white light emitting LEDs and the other parts mentioned above and make the moulded light guide 115 using a blue coloured clear polycarbonate to have the filtering effect.

Still further a moulded light guide as disclosed in the Indian patent application number 202041055180 dated Dec. 18, 2020, the contents of which are incorporated herein by reference, may be used in the disclosed system 100 with suitable modifications. For example, the moulded light guide may be used made with blue polycarbonate with the required blue filtering characteristics, as described herein. The person of ordinary skill in the art will notice that then only blue light emitting LEDs may be used as described previously. Or alternate ellipsoidal cavities therein may be coated with a blue filtering dye of the required characteristics to eliminate the planar annular emission filter 125. This will be necessary because, in the moulded light guide disclosed by the cited application, there are ellipsoidal cavities within which the LEDs 120 need to be located and an planar annular emission filter 125 would obstruct that. All such modifications described above and others that follow the principles on which the present disclosure is based shall be deemed to be embodiments of the present disclosure.

While specific language has been used to describe the disclosure, any limitations arising on account of the same are not intended. As would be apparent to a person skilled in the art, various working modifications may be made to the method in order to implement the inventive concept as taught herein.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

We claim:

1. An imaging system (100) configured for carrying out dual functions of fundus fluorescein angiography on a preterm baby subject and fundus imaging on a subject's eye (105), the system (100) characterized by: an injection molded light guide (115) based annular light source; a source of light for the light guide, the source of light comprising a plurality of LEDs (120), the plurality of LEDs (120) being arranged in a circle—wherein, alternate LEDs are blue light emitting LEDs and white light emitting LEDs; a planar annular emission filter (125) positioned between the light guide (115) and the plurality of LEDs (120) for filtering the light emitted by the blue light emitting LEDs to reach the light guide (115) and for allowing light emitted by the white light emitting LEDs to reach the light guide (115) unfiltered; a green barrier filter (146), for filtering light reflected by the fundus of the subject's eye, before the light reaching an image sensor (150), and wherein the position of the green barrier filter (146) is motor controlled for inserting and removing the green barrier filter (146) from the optical axis of the imaging optics (130); an aperture unit (136) for controlling an amount of light reaching the image sensor (150); a liquid lens (141), a focal length of which may be varied by applying one or more voltages to electrodes of the liquid lens (141), for focusing an image on the image sensor (150); an imaging optics (130) comprising a plurality of lenses (581 to 586) configured for focusing an image of the fundus of the subject's eye (105), wherein the lenses (581 to 586) are lenses that bend light rays equally at either surface of each lens for producing a low distortion image on the image sensor (150); and a control unit (175) configured at least for receiving user inputs for selecting one of white light emitting LEDs and blue light emitting LEDs from the plurality of LEDs (120), focusing the image on the image sensor (150) through controlling the liquid lens (141), and inserting or removing the green barrier filter from the optical axis of the imaging optics (130).

2. The system (100) as claimed in claim 1, wherein the planar annular emission filter (125) for filtering blue light has a low pass characteristic.

3. The system (100) as claimed in claim 1, wherein the planar annular emission filter (125) for filtering blue light has a low pass characteristic suppressing light of wavelengths above 500 nm.

4. The system (100) as claimed in claim 1, wherein the green barrier filter (146) has high pass characteristics.

5. The system (100) as claimed in claim 1, wherein the green barrier filter (146) has high pass characteristics suppressing all wavelengths below 515 nm.

6. The system (100) as claimed in claim 1, comprises a control unit (175) for receiving user inputs and executing one more functions selected from a list of functions comprising, but not limited to, energising blue light emitting LEDs only or white light emitting LEDs only from plurality of LEDs (120), raising or lowering the aperture of the mechanical iris (136, 536), raising or lowering the focal length of a liquid lens (141, 541), inserting or removing a green barrier filter (146, 546) from the optical axis of the imaging optics (130, 530).

\* \* \* \* \*